(12) United States Patent
Sasso

(10) Patent No.: US 9,066,751 B2
(45) Date of Patent: *Jun. 30, 2015

(54) INSTRUMENTATION AND METHOD FOR MOUNTING A SURGICAL NAVIGATION REFERENCE DEVICE TO A PATIENT

(75) Inventor: Ricardo Sasso, Carmel, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 771 days.

This patent is subject to a terminal disclaimer.

(21) Appl. No.: 13/351,627

(22) Filed: Jan. 17, 2012

(65) Prior Publication Data

US 2012/0197266 A1 Aug. 2, 2012

Related U.S. Application Data

(60) Division of application No. 10/967,655, filed on Oct. 18, 2004, now Pat. No. 8,180,429, which is a continuation of application No. PCT/US03/11610, filed on Apr. 15, 2003, which is a continuation-in-part of application No. 10/124,291, filed on Apr. 17, 2002, now Pat. No. 6,993,374.

(51) Int. Cl.
*A61B 5/05* (2006.01)
*A61B 17/34* (2006.01)
*A61B 19/00* (2006.01)

(52) U.S. Cl.
CPC ....... *A61B 17/3468* (2013.01); *A61B 2019/527* (2013.01); *A61B 2019/5483* (2013.01)

(58) Field of Classification Search
USPC .................................................. 600/424, 429
See application file for complete search history.

(56) References Cited

U.S. PATENT DOCUMENTS

| | | | |
|---|---|---|---|
| 6,725,080 B2 * | 4/2004 | Melkent et al. | 600/424 |
| 6,738,657 B1 * | 5/2004 | Franklin et al. | 600/429 |
| 6,856,828 B2 * | 2/2005 | Cossette et al. | 600/429 |
| 2002/0077540 A1 * | 6/2002 | Kienzle, III | 600/424 |

* cited by examiner

*Primary Examiner* — Peter Luong
(74) *Attorney, Agent, or Firm* — Sorell Lenna & Schmidt LLP

(57) ABSTRACT

Instrumentation and methods are provided for mounting a surgical navigation reference frame to a patient. A trocar may be positioned within a cannula to form an insertion device adapted for percutaneous introduction into the patient. A bone anchor having a bone engaging portion is inserted through the cannula for anchoring to bone. The bone anchor cooperates with the cannula to form a mounting device adapted for coupling with the surgical navigation reference frame. An image-guided surgical procedure may be performed at a location remote from the anchoring location. In a specific embodiment, a minimally invasive surgical procedure is performed, with a reference frame anchored to the pelvic bone, and more specifically to the iliac region of the pelvic bone. A second reference frame may be anchored to the femur.

34 Claims, 11 Drawing Sheets

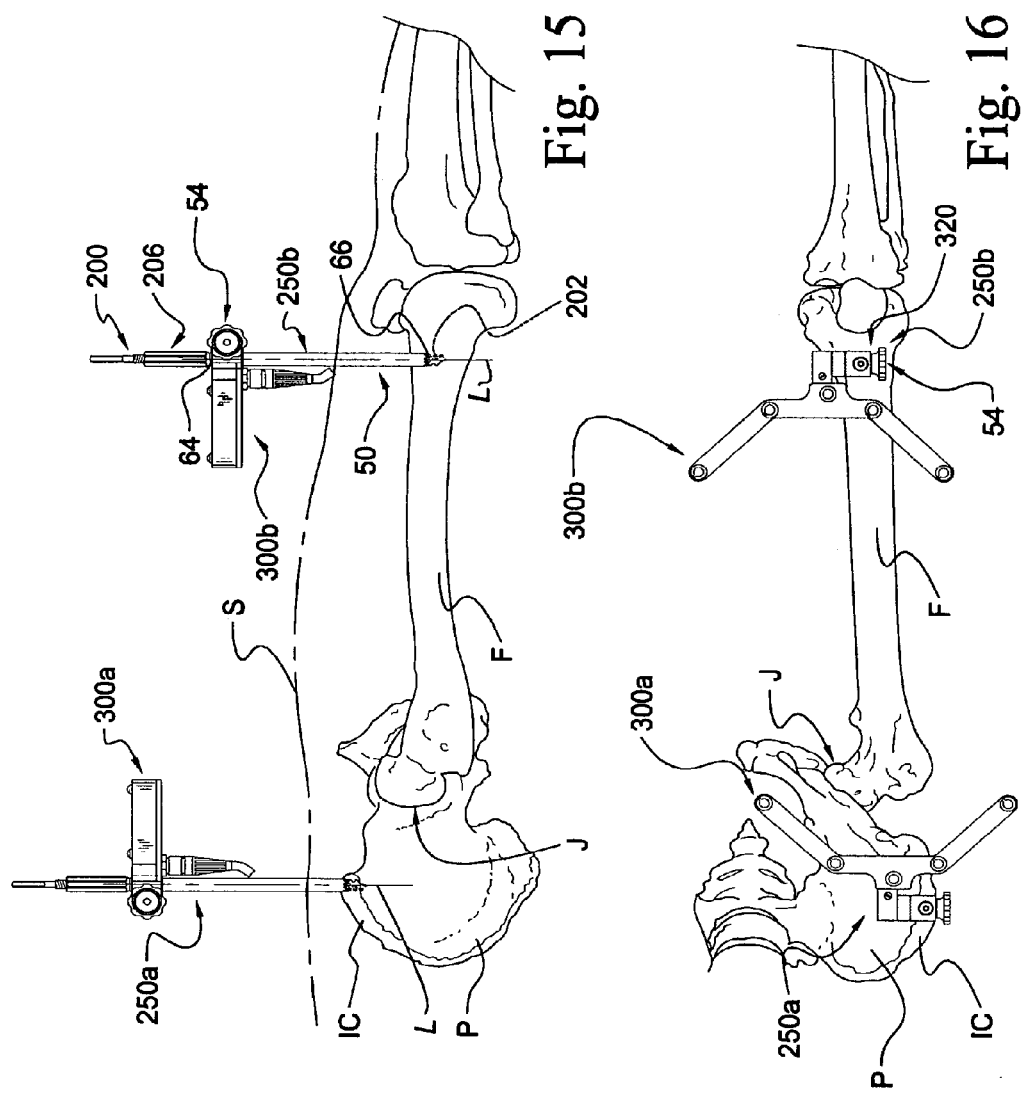

INSTRUMENTATION AND METHOD FOR MOUNTING A SURGICAL NAVIGATION REFERENCE DEVICE TO A PATIENT

CROSS REFERENCE TO RELATED APPLICATIONS

The present application is a divisional of U.S. patent application Ser. No. 10/967,655, filed Oct. 18, 2004, now U.S. Pat. No. 8,180,429 which is a continuation of PCT/US03/11610, filed Apr. 15, 2003, which is a continuation-in-part of U.S. patent application Ser. No. 10/124,291, filed Apr. 17, 2002, now U.S. Pat. No. 6,993,374 the contents of each of which are hereby incorporated by reference in their entirety.

FIELD OF THE INVENTION

The present invention relates generally to the field of surgical instrumentation and methods that utilize image navigation systems to indicate and track the relative position of various anatomical body parts and/or surgical instruments during medical and surgical procedures, and more specifically relates to instrumentation and methods for percutaneously mounting a surgical navigation reference device to a patient.

BACKGROUND OF THE INVENTION

Image navigation technology has been developed to indicate and track the relative position of various body parts and surgical instrumentation and implants during medical and surgical procedures. Image navigation systems typically utilize scans obtained either prior to or during a medical or surgical procedure to generate two-dimensional or three-dimensional images of various parts of the body. Such images aid the surgeon in manipulating and guiding surgical instruments, equipment and/or implants during various medical or surgical procedures. Interest in image navigation technology has increased as a result of recent advances in scanning technology, particularly with regard to technological advancements in devices that use computers to generate three-dimensional images, such as computed tomography (CT) or magnetic resonance imaging (MRI).

In the past, use of image navigation technology has been primarily directed to applications involving image guidance systems relating to the cranium. In such applications, the skull provides a convenient reference point for rigid attachment of an image navigation reference device, such as, for example, a surgical navigation reference frame. Recently, image navigation technology has been applied to other areas of the body including the spinal column. Surgical procedures involving the spinal column may be used, for example, to stabilize and/or fuse portions of the spine or to correct various spinal deformities or degenerative conditions. A number of surgical navigation systems have been developed for specific application to surgical procedures involving the spinal column. U.S. Pat. No. 6,226,548 to Foley et al. discloses one such system. A similar system is disclosed in U.S. Pat. No. 6,236,875 to Bucholz et al.

As illustrated in FIG. 1, surgical procedures involving the spine typically require the formation of a relatively large surgical incision I through the skin S of the patient adjacent the portion of the spinal column to be treated, usually extending along two or more levels of vertebrae V. The size of the surgical incision I must be large enough to accommodate for the manipulation and/or placement of various surgical instruments and implants required for the surgical procedure. Additionally, if image navigation technology is to be used in association with the surgical procedure, the surgical incision I must also accommodate for the mounting of a reference frame or registration device to the spinal column.

As illustrated in FIG. 2, the size of the surgical incision I must be large enough to permit anchoring of an image navigation reference frame or registration device 20 to at least one of the vertebrae $V_A$. The reference frame 20 is typically anchored to the vertebra $V_A$ via a bone clamp 22 having at least two opposing blades or jaws 24 which include inwardly-facing pointed tips or teeth 26 that provide secure engagement with vertebral bone. The blades 24 are typically clamped about the spinous process 28 of the vertebra $V_A$ to maintain the reference frame 20 in a substantially fixed position relative to the vertebra $V_A$. The blades 24 are sized to receive the bulb-shaped portion of the spinous process 28 therebetween and the teeth 26 are configured to penetrate into bone tissue for secure fixation thereto. However, if teeth 26 are used to secure the clamp 22 to the vertebra $V_A$, care must be taken to avoid damage or trauma to the vertebral bone. This is of particular concern when dealing with patient's having soft bone material, such as might be found in older patients or patients afflicted with a bone weakening disease (e.g., osteoporosis). Alternatively, one or more fasteners (not shown) may be used to anchor the reference frame 20 to the vertebra $V_A$ via insertion into the spinous process 28. However, the use of fasteners to anchor the reference frame 20 to the vertebra $V_A$ requires precise placement to avoid damage to adjacent neural structures, blood vessels and delicate tissue. Moreover, the use of fasteners may result in increased trauma to the vertebra $V_A$. A fiducial array 30 may also be anchored to the vertebra $V_A$ via the bone clamp 22. The fiducial array 30 provides feedback to the surgical navigation system regarding the precise location of the vertebra $V_A$ by touching a pointed surgical tracker (not shown) against various reference points along the fiducial array 30.

As also illustrated in FIG. 2, mounting of the reference frame 20 directly to the patient's spinal column creates a structural obstruction directly above and around the surgical site that could potentially interfere with or hinder the surgeon during the surgical procedure. Notably, mounting the reference frame 20 to the patient's spinal column must be done in an intra-procedural setting, subsequent to formation of the surgical incision I and commencement of surgery, thereby tending to increase the overall length of the surgical procedure. Moreover, after forming the surgical incision I, the surgeon must stand by and wait while other medical personnel acquire radiographic images of the patient's spinal column. The relatively lengthy wait encountered by the surgeon during this surgical procedure results in inefficient use of the surgeon's time. Additionally, since acquisition of the radiographic images must be done in an intra-operative setting, there is a higher risk of potential infection because the incision must be open for a relatively lengthy period of time.

As discussed above, the use of image navigation systems in surgical procedures involving the spinal column typically requires the formation of a relatively large surgical incision. Large surgical incisions are highly invasive and can result in increased trauma, blood loss, post-operative pain, and a lengthy recovery period. It would therefore be desirable to provide instrumentation and methods for the mounting of an image navigation reference frame to the patient in a minimally invasive manner to reduce the size of the surgical incision, or by eliminating the surgical incision entirely in applications involving fluoroscopic surgery or percutaneous surgical procedures. It would also be desirable to mount the image navigation reference frame to the patient at a location remote from the surgical site to eliminate structural obstructions above and proximately adjacent the surgical site, thereby providing the surgeon with a relatively unobstructed area to perform the surgical procedure. Moreover, it would be desirable to mount the image navigation reference frame to the patient in a pre-procedural setting at a time prior to formation of the surgical incision and commencement of surgery, thereby reducing the overall length of the surgical procedure and the risks associated therewith. Mounting the reference frame to the patient in a pre-procedural setting would also allow the acquisition of radiographic images without the hindrance of surgical drapes.

Thus, there is a general need in the industry to provide improved surgical instrumentation and methods for mounting a surgical navigation reference device to a patient than is currently available within the industry. The present invention meets this need and provides other benefits and advantages in a novel and unobvious manner.

SUMMARY OF THE INVENTION

The present invention relates generally to instrumentation and methods for mounting a surgical navigation reference device to a patient. While the actual nature of the invention covered herein can only be determined with reference to the claims appended hereto, certain forms of the invention that are characteristic of the preferred embodiments disclosed herein are described briefly as follows.

In one form of the present invention, a method is provided for mounting a surgical navigation reference device to a patient for performing an image-guided surgical procedure adjacent the patient's spinal column. The method is comprised of the following steps: providing a bone anchor; anchoring the bone anchor to bone at a location remote from the patient's spinal column; coupling the reference device to the bone anchor to mount the reference device in a substantially fixed position relative to the patient's spinal column; and performing an image-guided surgical procedure adjacent the patient's spinal column.

In another form of the present invention, a method is provided for mounting a surgical navigation reference device to a patient for performing an image-guided surgical procedure adjacent the patient's hip joint. The method is comprised of the following steps: providing first and second bone anchors; anchoring the first bone anchor to a portion of the patient's pelvic bone; coupling a first reference device to the first bone anchor to mount the first reference device in a substantially fixed position relative to the pelvic bone; anchoring the second bone anchor to a portion of the patient's femur; coupling a second reference device to the second bone anchor to mount the second reference device in a substantially fixed position relative to the femur; and performing an image-guided surgical procedure adjacent the patient's hip joint.

In another form of the present invention, a method is provided to mount a surgical navigation reference device to a patient for performing an image-guided surgical procedure. The method is comprised of the following steps: providing a cannula having a proximal end and a distal end, a trocar having a distal end portion, and a bone anchor having a bone engaging portion; positioning the trocar within the cannula with the distal end portion of the trocar extending beyond the distal end of the cannula; percutaneously introducing the cannula into the patient; removing the trocar from the cannula; inserting the bone engaging portion of the bone anchor through the cannula; anchoring the bone engaging portion of the bone anchor to bone; and coupling the surgical navigation reference device to the bone anchor.

In another form of the present invention, instrumentation is provided for performing an image-guided surgical procedure on a patient. The instrumentation is comprised of a cannula having a proximal end and a distal end; a trocar positioned within the cannula with a distal end portion extending beyond the distal end of the cannula to form an insertion device adapted for percutaneous introduction into the patient; and a bone anchor having a bone engaging portion insertable through the cannula and adapted for anchoring to bone. The bone anchor cooperates with the cannula to form a mounting device, with the surgical navigation reference device adapted for coupling thereto to percutaneously mount the reference device to the patient.

It is one object of the present invention to provide improved instrumentation and methods for mounting a surgical navigation reference device to a patient.

Further objects, features, advantages, benefits, and aspects of the present invention will become apparent from the drawings and description contained herein.

BRIEF DESCRIPTION OF THE DRAWINGS

FIG. 15 is a side view of the pelvic and femoral regions of a patient, illustrating percutaneous anchoring of the surgical navigation reference device illustrated in FIGS. 9 and 10 to the iliac crest of the pelvic bone and to the lower portion of the femur.

FIG. 16 is a top view of the patient illustrated in FIG. 15, illustrating percutaneous anchoring of the surgical navigation reference devices to the iliac crest of the pelvic bone and to the lower portion of the femur.

DESCRIPTION OF THE ILLUSTRATED EMBODIMENTS

Figure 1:
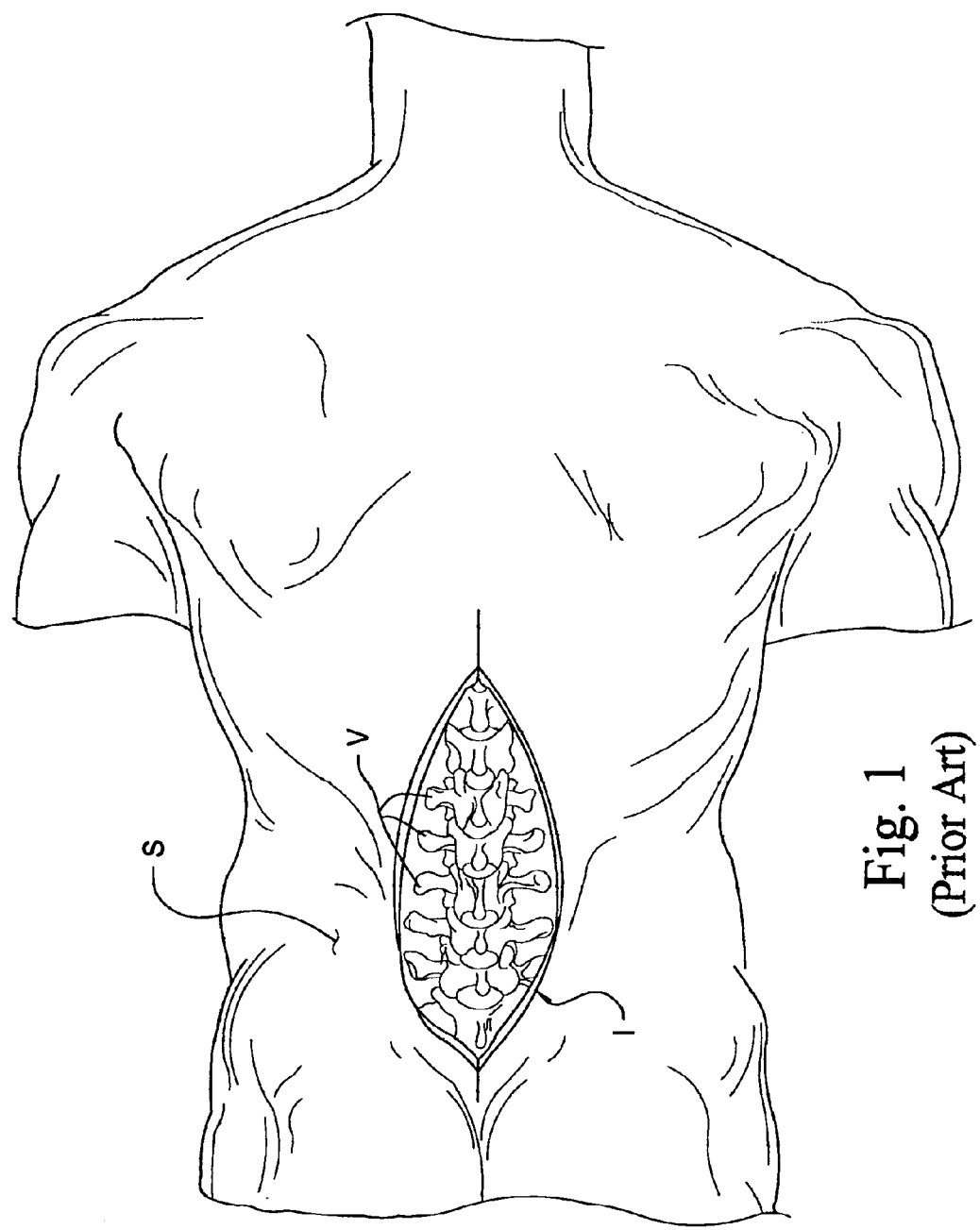
FIG. 1 is a top view of the back of a patient lying in a prone position, illustrating the formation of a surgical incision above the lumbar region of the spinal column to accommodate a prior art method and apparatus for mounting a surgical navigation reference device to the patient's spinal column.

For the purposes of promoting an understanding of the principles of the invention, reference will now be made to the embodiments illustrated in the drawings and specific language will be used to describe the same. It will nevertheless be understood that no limitation on the scope of the invention is hereby intended, and that alterations and further modifications in the illustrated devices and further applications of the principles of the invention as illustrated herein are contemplated as would normally occur to one skilled in the art to which the invention relates.

Referring to FIGS. 3-8, shown therein is surgical instrumentation according to one form of the present invention for use in association with the percutaneous mounting of a surgical navigation reference device to a patient. Although the instrumentation and methods illustrated and described herein are directed to surgical procedures involving the spinal column, it should be understood that applications of the present invention may extend to surgical procedures outside of the spinal field, including surgical procedures involving the cranium, other types of bones, and/or other anatomical components.

Figure 3:
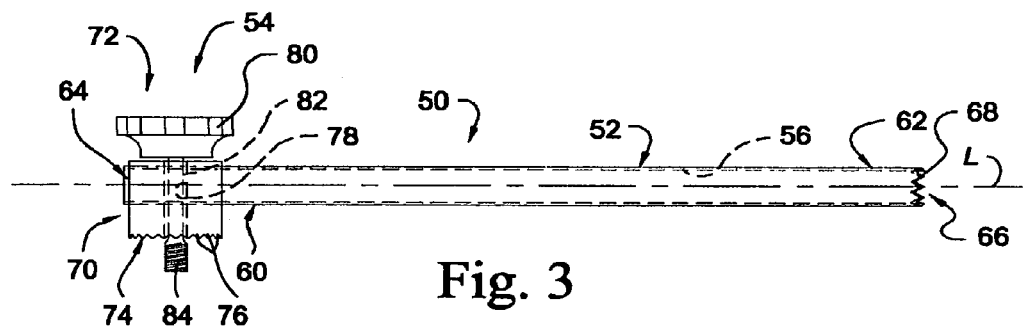
FIG. 3 is a top view of a cannula according to one embodiment of the present invention for use in association with the mounting of a surgical navigation reference device to a patient.
Figure 4:
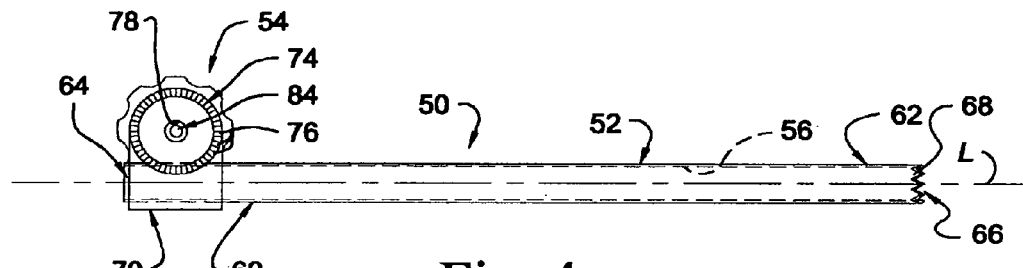
FIG. 4 is a side view of the cannula illustrated in FIG. 3.

Referring specifically to FIGS. 3 and 4, shown therein is a cannula 50 according to one embodiment of the present invention. The cannula 50 extends along a longitudinal axis L and is generally comprised of an elongate tube 52 and a coupling mechanism 54. The elongate tube 52 defines a passage 56 formed entirely therethrough and extending generally along the longitudinal axis L. As will be discussed in further detail below, the axial passage 56 provides a percutaneous passageway or portal for insertion of a bone anchor into the patient for subsequent anchoring to bone. Although the cannula tube 52 is illustrated as having a cylindrical configuration, it should be understood that other shapes and configurations are also contemplated as falling within the scope of the invention. As will also be discussed in further detail below, the coupling mechanism 54 is adapted for engagement with an image navigation reference device to mount the image navigation reference device in a substantially fixed position relative to the patient's bone.

The elongate tube 52 of the cannula 50 includes a proximal end portion 60 and a distal end portion 62. The coupling mechanism 54 is preferably attached to the proximal end portion 60 of the tube 52, with the proximal-most end 64 of the tube 52 extending beyond the coupling mechanism 54. The distal end portion 62 of the tube 52 includes a distal-most end 66 that preferably includes one or more anchoring elements 68 configured for contacting and engaging bone to prevent or at least inhibit displacement of the cannula 50 relative to the bone. In one embodiment of the invention, the anchoring elements 68 are serrated teeth extending about the periphery of the distal end 66 of the tube 52. However, it should be understood that other types and configurations of anchoring elements 68 are also contemplated, including a V-shaped wedge configuration or a crescent-shaped configuration. It should also be understood that the distal end 66 of the tube 52 could alternatively define a substantially flat configuration.

The coupling mechanism 54 of the cannula 50 is generally comprised of a mounting block 70 and a fastener 72. The mounting block 70 is preferably attached to the proximal end portion 60 of the tube 52. The mounting block 70 includes a laterally-facing surface 74 that preferably defines a plurality of uniformly spaced, radially-extending splines 76 arranged in a generally circular pattern. An opening 78 extends through the mounting block 70 and is preferably centrally located relative to the circular pattern of radially-extending splines 76. The fastener 72 includes a head 80 and a stem 82, with the stem 82 extending through the opening 78 in the mounting block 70. The head 80 is preferably over-sized so as to define a thumb-screw arrangement to aid the surgeon in grasping and manipulating the fastener 72. At least the distal end portion 84 of the stem 82 is threaded, the purpose of which will become apparent below.

Figure 5:
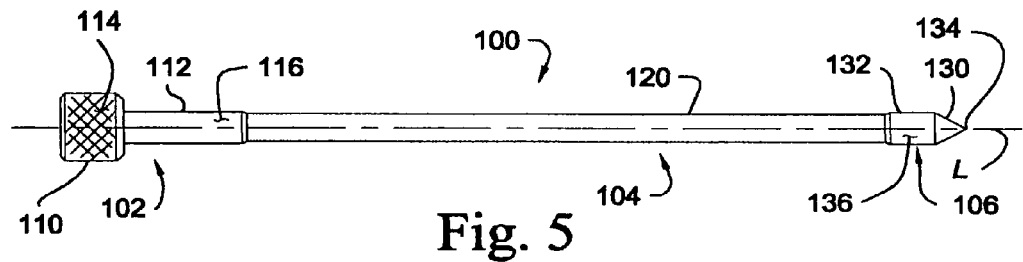
FIG. 5 is a side view of a trocar according to one embodiment of the present invention for use in association with the cannula illustrated in FIG. 3, as used to percutaneously introduce the cannula into the patient.

Referring to FIG. 5, shown therein is a trocar 100 according to one embodiment of the present invention. The trocar 100 extends generally along the longitudinal axis L and includes a proximal end portion 102, an intermediate portion 104 and a distal end portion 106. The proximal end portion 102 preferably includes a stop member 110 and a guide member 112. The stop member 110 has an outer cross section sized somewhat larger than the inner cross section of the axial passage 56 of the cannula tube 52. Additionally, the stop member 110 preferably defines a roughened outer surface 114 to aid the surgeon in grasping and manipulating the trocar 100. In one embodiment, the roughened outer surface 114 is formed by knurling. The guide member 112 preferably defines a relatively smooth outer surface 116 sized and shaped to be slidably received within the axial passage 56 of the cannula tube 52. The intermediate portion 104 is preferably configured as a solid shaft member 120. The distal end portion 106 preferably includes a tip portion 130 and a guide member 132. In a preferred embodiment of the invention, the distal tip portion 130 has a conical-shape defining a pointed tip 134 to facilitate percutaneous insertion through the skin of the patient. However, it should be understood that the distal tip portion 130 can take on other configurations, including a bullet-shape configuration defining a blunted tip to minimize trauma to adjacent tissue. The guide member 132 preferably defines a relatively smooth outer surface 136 sized and shaped to be slidably received through the axial passage 56 of the cannula tube 52.

Figure 6:
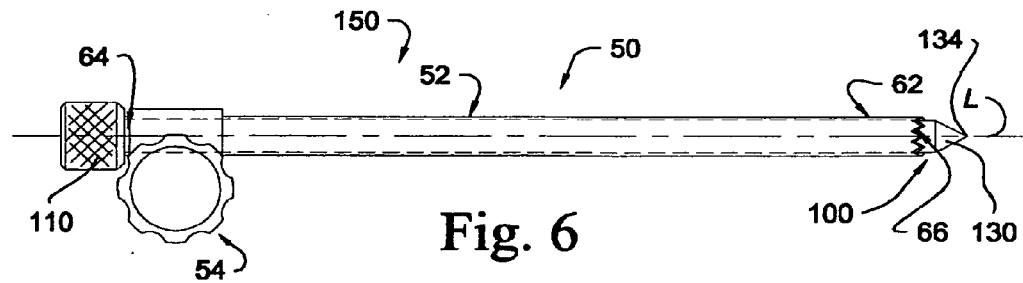
FIG. 6 is a side view of an insertion instrument according to one embodiment of the present invention, illustrating insertion of the trocar within the cannula.

Referring to FIG. 6, shown therein is the trocar 100 positioned within the cannula 50 to form a percutaneous insertion instrument 150 according to one embodiment of the present invention. The trocar 100 has a length sized to allow the distal tip 130 to extend beyond the distal end 66 of the cannula tube 52. Specifically, the trocar 100 is inserted through the axial passage 56 of the cannula tube 52 until the stop member 110 abuts the proximal end 64 of the cannula tube 52. The stop member 110 thereby ensures proper positioning of the distal tip 130 of the trocar 100 relative to the distal end 66 of the cannula 50. In an alternative embodiment of the invention, the stop member 110 may abut the proximally-facing surface of the cannula mounting block 70 to properly position the trocar 100 relative to the cannula 50. As will be discussed below, when the trocar 100 is properly positioned within the cannula 50, the resulting insertion instrument 150 may be introduced into the patient via percutaneous insertion through the patient's skin. It should be understood that the insertion instrument 150 may also be introduced into the patient via a preformed opening or incision through the patient's skin.

Figure 7:
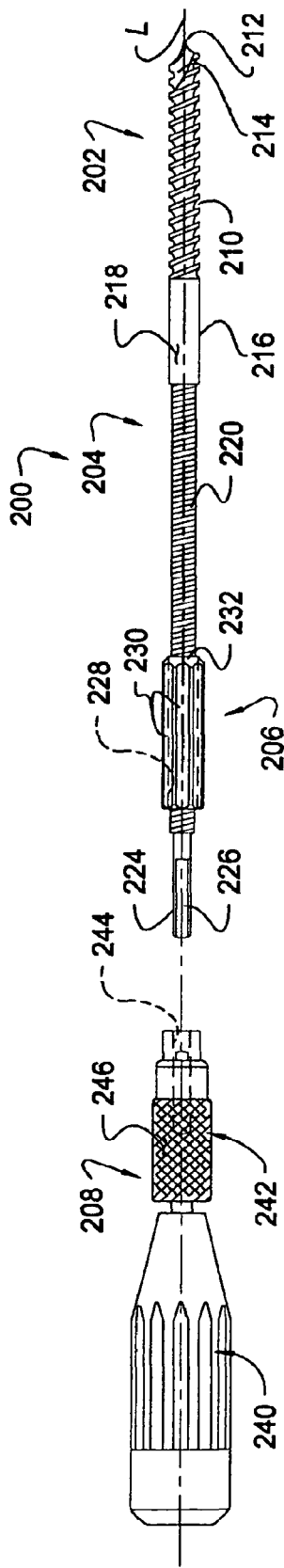
FIG. 7 is a side view of a bone anchor according to one embodiment of the present invention for use in association with mounting the surgical navigation reference device to the patient.

Referring to FIG. 7, shown therein is a bone anchor device 200 according to one embodiment of the present invention. The bone anchor device 200 extends along a longitudinal axis L and is generally comprised of a bone engaging portion 202, a shaft portion 204, a stop member 206, and a handle portion 208. As will be discussed in further detail below, the bone engaging portion 202 of the bone anchor 200 is insertable through the axial passage 56 of the cannula 50 for percutaneous engagement with bone. As will also be described in further detail below, the bone anchor 200 cooperates with the cannula 50 to form a mounting instrument suitable for rigidly mounting an image navigation reference device to the patient.

The bone engaging portion 202 of the bone anchor 200 preferably defines a series of threads 210. However, other means for engaging bone are also contemplated as would occur to one of skill in the art. In one embodiment of the invention, the threads 210 of the bone engaging portion 202 are configured to be self-tapping. In another embodiment of the invention, the threads 210 of the bone engaging portion 202 are configured to be self-drilling. The distal end portion of the bone engaging portion 202 preferably defines a pointed tip 212 to facilitate introduction and penetration into bone, and also preferably includes at least one flute 214 extending across one or more of the threads 210 to facilitate formation of an opening in the bone and the cutting of threads along the opening. In this manner, the bone engaging portion 202 may be engaged to the bone without having to pre-drill an opening and/or pre-cut threads along the opening.

The distal end portion of the shaft 204 preferably includes a guide member 216 that defines a relatively smooth outer surface 218 sized and shaped to be slidably received within the axial passage 56 of the cannula tube 52. The intermediate portion of the shaft 204 preferably includes machine threads 220 defined along a length thereof. The proximal end portion of the shaft 204 preferably includes a connecting portion 224 that defines one or more flats 226 configured for engagement with the handle portion 208.

The stop member 206 preferably includes a threaded axial passage 228 extending therethrough. The threaded axial passage 228 is configured to threadingly engage the machine threads 220 defined along the shaft 204. As should be appreciated, rotation of the stop member 206 about the longitudinal axis L will axially displace the stop member 206 along the shaft 204. In this manner, the axial position of the stop member 206 may be adjusted relative to the shaft 204 and the bone engaging portion 202, the purpose of which will become apparent below. The outer surface of the stop member 206 preferably includes a number of axial grooves 230 to aid the surgeon in grasping and rotating the stop member 206. In another embodiment of the invention, the outer surface of the stop member 206 may be roughened, such as, for example, by knurling. The distal end portion of the stop member 206 preferably defines a conically-shaped surface 232, the purpose of which will become apparent below.

The handle portion 208 preferably includes a handle 240 and a coupler 242 adapted to releasably couple the handle 240 to the proximal connecting portion 224 of the shaft 204. In one embodiment of the invention, the handle 240 has an axial configuration extending generally along the longitudinal axis L to allow the surgeon to effectively grasp and manipulate the bone anchor 200 and to facilitate driving of the bone engaging portion 202 into bone. However, other handle arrangements are also contemplated as would occur to one of ordinary skill in the art, such as, for example, a T-handle arrangement.

In one embodiment of the invention, the coupler 242 is configured similar to a quick disconnect (QD-type) fitting, whereby axial displacement of the coupler 242 permits the handle 240 to be selectively inserted onto and removed from the shaft 204. Specifically, the coupler 242 defines an axial opening 244 sized to receive the proximal connecting portion 224 of the shaft 204 therein. One or more engaging elements (not shown), such as a number of spherical-shaped balls, are releasably engaged against the flats 226 defined along the connecting portion 224 to releasably connect the handle portion 208 to the shaft 204. The engaging elements (not shown) may be disengaged from the flats 226 via axial displacement of the coupler 242 away from the handle 240, thereby allowing the handle portion 208 to be selectively removed from the shaft 204. The outer surface 246 of the coupler 242 is preferably roughened, such as by knurling, to allow the surgeon to effectively grasp and axially displace the coupler 242.

Figure 8:
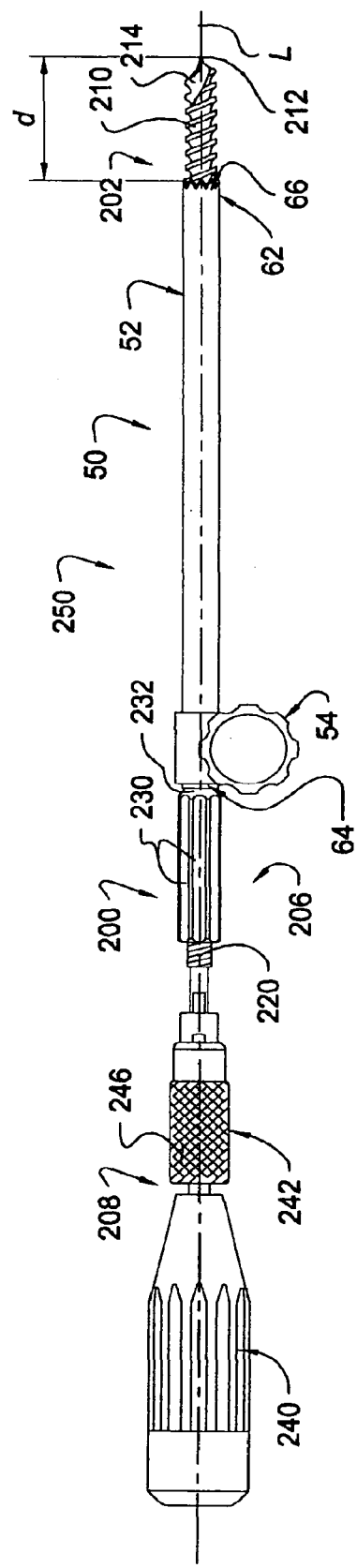
FIG. 8 is a side view of a mounting instrument according to one embodiment of the present invention, illustrating insertion of the bone anchor within the cannula.

Referring to FIG. 8, shown therein is the bone anchor 200 inserted within the cannula 50 to form a mounting instrument 250 according to one embodiment of the present invention. The bone anchor 200 has a length that is sized to allow the bone engaging portion 202 to extend beyond the distal end 66 of the cannula tube 52. Moreover, the distance d that the bone engaging portion 202 is permitted to extend beyond the distal end 66 of the cannula tube 52 is limited by abutment of the adjustable stop member 206 against the proximal end 64 of the cannula tube 52. In this manner, the adjustable stop member 206 prevents under insertion and over insertion of the bone engaging portion 202 into bone. As discussed above, rotation of the adjustable stop member 206 correspondingly displaces the adjustable stop member 206 along the shaft 204.

It should be appreciated that adjustment of the axial position of the stop member 206 will correspondingly adjust the distance d that the bone engaging portion 202 is permitted to extend beyond the distal end 66 of the cannula tube 52. The conically-shaped surface 232 of the adjustable stop member 206 is partially engaged within the proximal end portion 64 of the cannula tube 52 to securely engage the bone anchor 200 with the cannula 50, thereby providing a substantially rigid mounting instrument 250. Engagement of the conically-shaped surface 232 against the proximal end portion 64 of the cannula tube 52 also aids in co-axially aligning the bone anchor 200 with the cannula 50. In an alternative embodiment of the invention, the stop member 206 may abut the proximally-facing surface of the cannula mounting block 70 to limit the distance d that the bone engaging portion 202 is permitted to extend beyond the distal end 66 of the cannula tube 52.

Figures 9, 10:
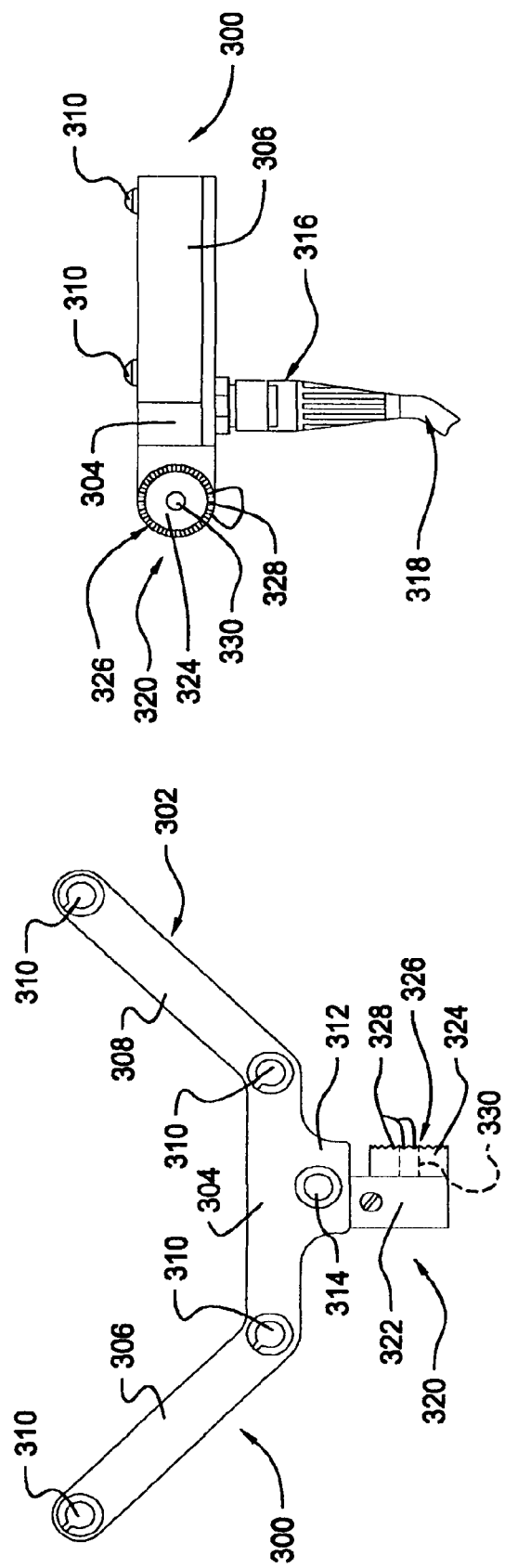
FIG. 9 is a top view of a surgical navigation reference device according to one embodiment of the present invention.
FIG. 10 is a side view of the surgical navigation reference device illustrated in FIG. 9.

Referring to FIGS. 9 and 10, shown therein is a surgical navigation reference device 300. In one embodiment of the invention, the surgical navigation reference device 300 is a reference frame assembly or another type of reference device suitable for use in association with image navigation systems. In one embodiment, the reference frame 300 is of the passive-type; however, use of an active-type reference frame is also contemplated as falling within the scope of the present invention. The operation and function of the reference frame 300 would be readily apparent to one of skill in the art and therefore need not be discussed in detail herein.

In the illustrated embodiment, the reference frame 300 has a U-shaped or arc-shaped configuration; however, other suitable shapes and configurations are also contemplated as falling within the scope of the invention. Although a specific embodiment of an image navigation reference frame has been illustrated and described herein, it should be understood that other types and configurations of image navigation reference frames are also contemplated, and that the specific embodiment of the reference frame 300 has been included for illustrative purposes only and does not in any way limit the scope of the present invention. Other types and configurations of image navigation reference frames suitable for use in association with the present invention are illustrated and described in U.S. Pat. No. 6,226,548 to Foley et al. and U.S. Pat. No. 6,236,875 to Burcholz et al., the contents of which are hereby expressly incorporated by reference in their entirety.

As shown in FIGS. 9 and 10, the reference frame 300 includes a U-shaped frame member 302 having a base portion 304 and a pair of leg portions 306, 308 extending from opposite ends of the base portion 304. The U-shaped frame member 302 includes a number of surgical navigation emitters 310 that provide a positive indication of position and/or movement during an image-guided surgical procedure. The emitters 310 are comprised of LEDs, reflective spherical balls, or any other type of surgical navigation emitter know to those of skill in the art. An emitter 310 is positioned adjacent the distal end of each leg potion 306, 308 and adjacent the interconnection location between the leg portions 306, 308 and the base portion 304. The base portion 304 includes a protuberance or shoulder 312 projecting therefrom in a direction generally opposite the leg portions 306, 308. A calibration divot 314 is centrally located on the shoulder 312. An electrical connector 316 is coupled to the shoulder 312 opposite the calibration divot 314 for connection with an electrical cable 318 (FIG. 10). The cable 318 electrically couples the emitters 310 and the calibration divot 314 to an image navigation control unit (not shown). In another embodiment of the invention, the reference frame 300 may be battery-operated such that no electrical cable 318 is required to directly couple the reference frame 300 to the image navigation control unit.

A coupling mechanism 320 extends from the shoulder 312 and is configured for releasable interconnection with the coupling mechanism 54 of the cannula 50. The coupling mechanism 320 generally includes a block portion 322 and a washer portion 324. The block portion 322 is operatively attached to the shoulder 312, with the washer portion 324 extending laterally from the block portion 322. The washer portion 324 includes a laterally-facing engaging surface 326 defining a plurality of uniformly spaced, radially-extending splines 328 arranged in a circular pattern about the outer periphery of the washer portion 324. The radially-extending splines 328 are configured for interdigitating engagement with the radially-extending splines 76 of the cannula coupling mechanism 54. As will be discussed below, such interdigitating engagement allows the reference frame 300 to be variably positioned at a select angular orientation relative to the longitudinal axis L of the mounting device 250. The washer portion 324 also defines a threaded opening 330 configured to threadingly receive the threaded fastener portion 84 of the cannula coupling mechanism 54 therein to releasably couple the reference frame 300 to the cannula 50. Although a specific embodiment of the coupling mechanism 320 has been illustrated and described herein, it is contemplated that other types and configurations of coupling mechanisms may be used to releasably couple the reference frame 300 to the cannula 50.

As would be appreciated by those of skill in the art, the reference frame 300 cooperates with other components of an image navigation system to provide computer-assisted, image-guided surgery. More specifically, a digital image is generated and displayed on a monitor (not shown) for viewing by the surgeon before and/or during a medical or surgical procedure. The digital image represents at least one anatomical element, such as, for example, a vertebral body, and is produced from an image data set that is typically generated in a pre-operative or pre-procedural setting by a CAT scan or an MRI. The image data set includes multiple reference points corresponding to various portions of the anatomical element. The image navigation system typically includes a digitizer or a sensor array for identifying the relative position of each of the reference points to be displayed by tracking the position of the emitters 310 disposed on the reference frame 300. The image navigation system also includes a processor, such as, for example, a programmable controller or another type of computer processor for modifying the image data set according to the identified relative position of each of the reference points during the surgical procedure. The position of a surgical instrument, such as, for example, a probe or drill, may also be tracked by the sensor array relative to the anatomical element. Further features and aspects regarding the componentry and the general operation and function of surgical navigation systems are well known to those of skill in the art and therefore need not be discussed in further detail herein.

Having described various embodiment of surgical instrumentation suitable for use in association with the percutaneous mounting of an image navigation reference frame to a patient, reference will now be made to a method for accomplishing the same. Referring to FIGS. 11-14, collectively shown therein is a method for percutaneously mounting the image navigation reference frame 300 to a patient according to one form of the present invention. The cannula 50, the trocar 100, the bone anchor 200 and the reference frame 300 are all initially sterilized as per standard operating practice. Pursuant to standard operating procedure, the patient is given a general anesthetic and is preferably secured in a relatively motionless position relative to a support structure, such as, for example, an operating table. A surgical positioning frame or another type of stabilizing device may be used to help maintain the patient in a fixed position and orientation during the mounting of the reference frame 300 and throughout the surgical procedure.

In a preferred embodiment of the invention, the image navigation reference frame 300 is anchored to bone at a location remote from the surgical site. In image-guided surgical procedures performed adjacent the patient's spinal column, the reference frame 300 is preferably anchored to bone at a location remote from the patient's spine. In one embodiment of the invention, the reference frame 300 is anchored to the patient's pelvic bone P, and more particularly the iliac region of the pelvic bone P. In a more specific embodiment of the invention, the reference frame 300 is anchored to the iliac crest IC of the pelvic bone P. Although the reference frame 300 has been illustrated and described as being mounted to certain portions and locations of the patient's anatomy, it should be understood that the reference frame 300 may be anchored to other skeletal members and positioned adjacent other anatomical components.

One advantage of anchoring the reference frame 300 to the patient's pelvic bone P, and more particularly to the iliac crest IC, is that such an anchoring technique will likely result in reduced trauma to the patient. Additionally, anchoring the reference frame 300 to the iliac crest IC or other portions of the pelvic bone P will typically require a lesser degree of accuracy and precision as compared with other anchoring techniques involving more delicate areas of the patient's anatomy, such as, for example, a vertebral body. As a result, the risk of injury or complications resulting from mounting of the reference frame 300 to the patient can be significantly reduced. For purposes of comparison, the prior art surgical navigation system illustrated in FIG. 2 teaches anchoring of the reference frame 20 directly to the vertebra $V_A$. As discussed above, engagement of the reference frame 20 to the spinous process 28 of the vertebra $V_A$ may result in damage or trauma to the vertebral bone, particularly when dealing with older patients or patients afflicted with bone weakening diseases. Moreover, engagement of the reference frame 20 directly to the vertebra $V_A$ requires a relatively high degree of precision and accuracy to avoid damage to adjacent neural structures, blood vessels and other delicate tissues.

Figure 11:
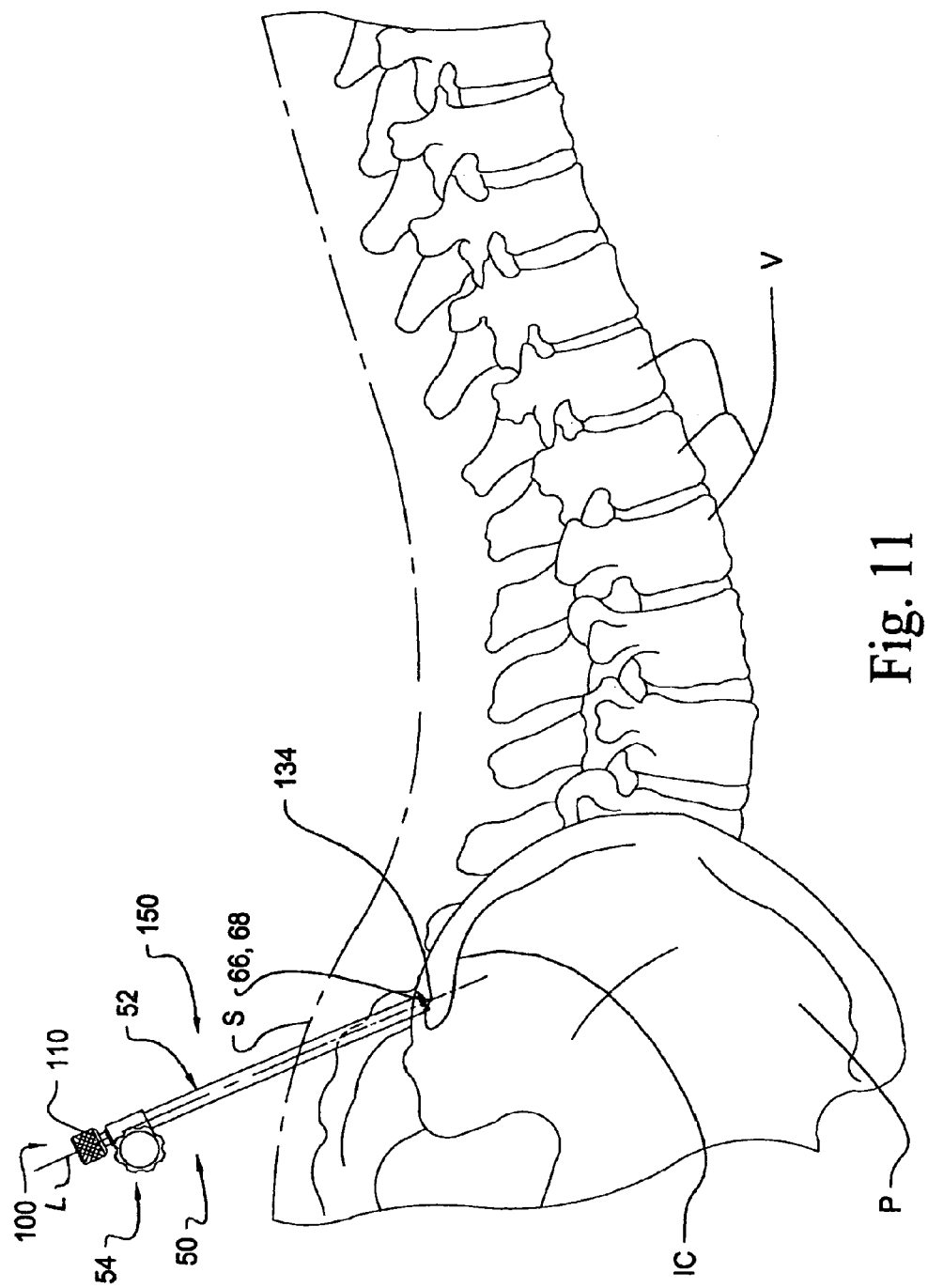
FIG. 11 is a side view of the spinal column of a patient, illustrating the percutaneous introduction of the insertion instrument illustrated in FIG. 6 into the patient, with the distal end of the insertion instrument positioned adjacent the iliac crest of the pelvic bone.

Referring to FIG. 11, shown therein is the insertion instrument 150 percutaneously introduced through the skin S of the patient and positioned adjacent the iliac crest IC of the pelvic bone P. Specifically, the trocar 100 is initially positioned within the cannula 50 with the trocar tip 130 extending beyond the distal end 66 of the cannula tube 52 to form the insertion instrument 150 (See FIG. 6). As would be apparent to one of skill in the art, the insertion instrument 150 may then be percutaneously introduced into the patient in a minimally invasive manner. As discussed above, in an alternative embodiment of the invention, the insertion instrument 150 may be introduced into the patient via a preformed opening or incision through the skin S Upon introduction of the insertion instrument 150 into the patient, the distal end 66 of the cannula tube 52 is preferably positioned in abutment against bone, with the teeth or serrations 68 securely engaging the bone to substantially prevent displacement of the cannula tube 52. Following the percutaneous introduction of the insertion instrument 150 into the patient, the trocar 150 is removed from the cannula 50, thereby establishing a percutaneous portal through the patient's skin S to a location adjacent the iliac crest IC of the pelvic bone P.

Figure 12:
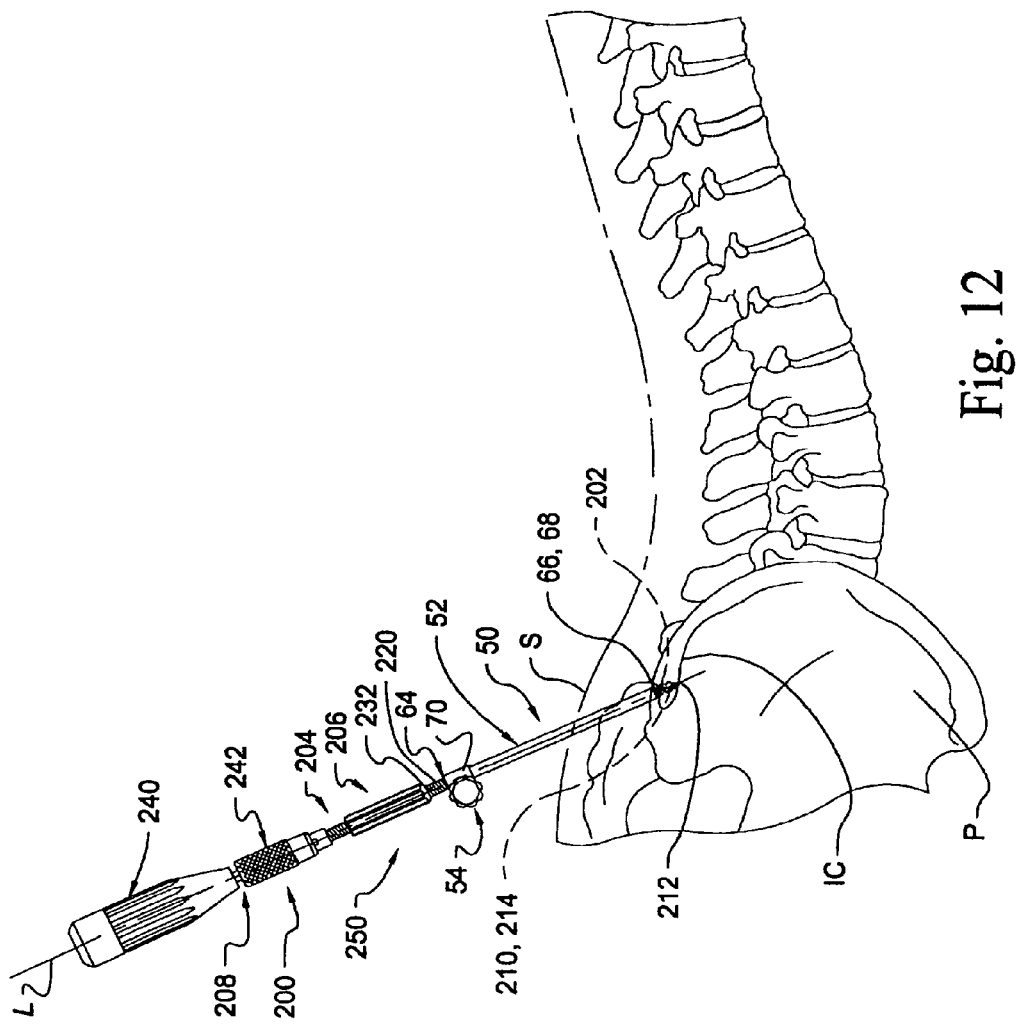
FIG. 12 is a side view of the spinal column of the patient illustrated in FIG. 11, illustrating insertion of the bone anchor through the cannula, with the bone engaging portion of the bone anchor threaded into the iliac crest of the pelvic bone.

Referring to FIG. 12, the bone engaging portion 202 of the bone anchor 200 is inserted through the percutaneous portal established by the cannula tube 52 and is anchored to the iliac crest IC. As discussed above, in one embodiment of the invention, the bone engaging portion 202 defines a series of threads 210, a pointed tip 212, and a flute 214 extending across one or more of the threads 210 (See FIG. 7). As a result, the bone engaging portion 202 is capable of forming a threaded opening in the bone without the need for additional surgical instrumentation such as a bone drill and/or a bone tap. In this manner, the bone engaging portion 202 is both self-drilling and self-tapping. However, it should be understood that other configuration of the bone engaging portion 202 are also contemplated as would occur to one of ordinary skill in the art, including configurations that do not have self-drilling and/or self-tapping features. The pointed tip 212 of the bone engaging portion 202 aids in initial penetration of the bone anchor 200 into bone and also facilitates threading advancement of the bone engaging portion 202 through the bone. The flute 214 extending across the threads 210 provides the bone engaging portion 202 with the capability to cut threads into the bone and to channel bone material and other debris out of the threading opening.

Once the pointed tip 212 is positioned against the bone, rotation of the handle 240 about the longitudinal axis L threadingly engages the bone engaging portion 202 into the iliac crest IC of the pelvic bone P. As discussed above, the distance d that the bone engaging portion 202 is permitted to extend beyond the distal end 66 of the cannula tube 52 is limited by abutment of the conical surface 232 of the adjustable stop member 206 against the proximal end 64 of the cannula tube 52 (See FIG. 8). In this manner, the adjustable stop member 206 prevents over-insertion and under-insertion of the bone engaging portion 202 relative to the bone. As should be appreciated, adjustment of the axial position of the adjustable stop member 206 will correspondingly adjust the distance d that the bone engaging portion 202 is permitted to extend beyond the distal end 66 of the cannula tube 52.

Figure 13:
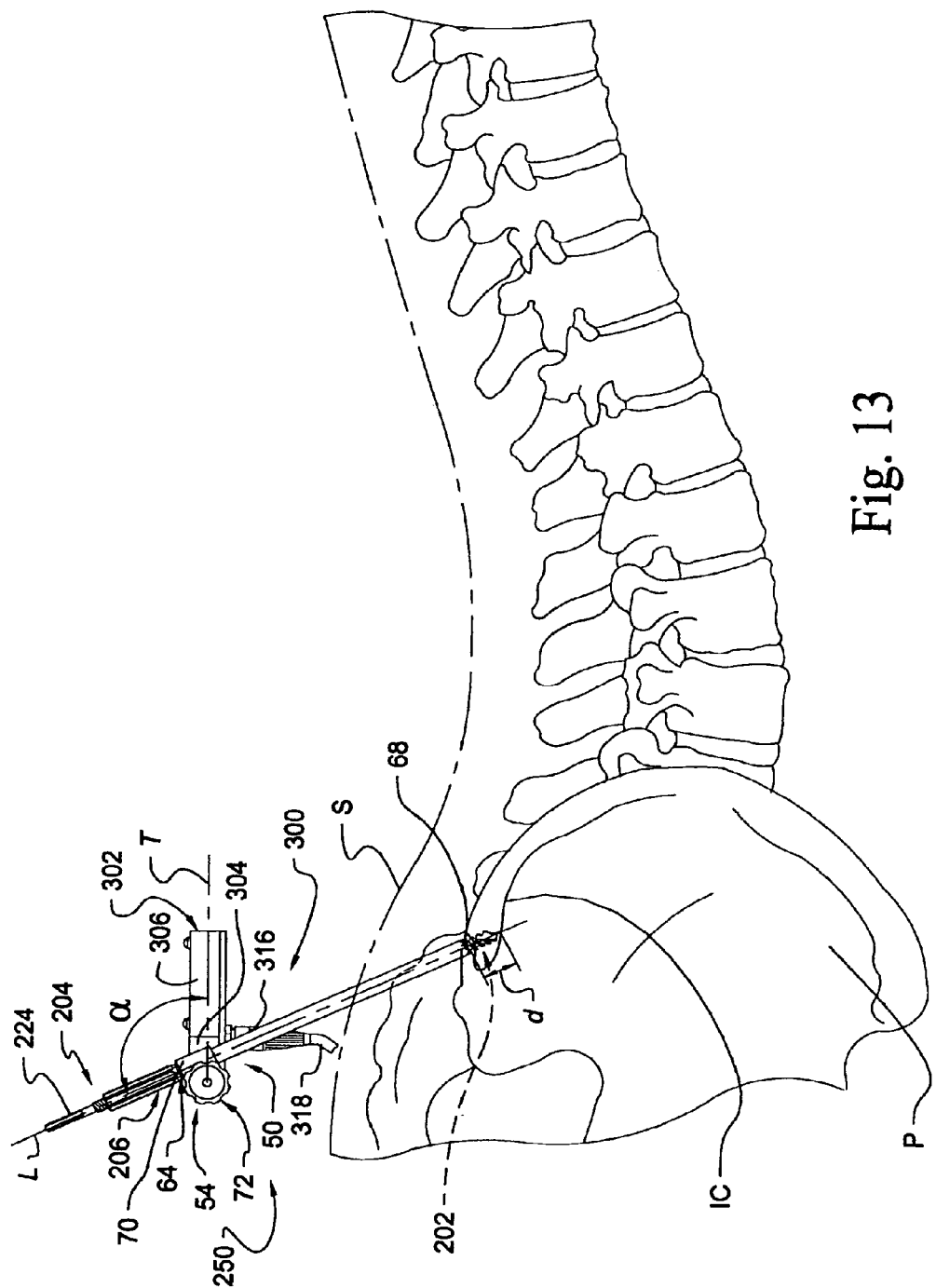
FIG. 13 is a side view of the spinal column of the patient illustrated in FIG. 11, illustrating coupling of the surgical navigation reference device illustrated in FIGS. 9 and 10 to the mounting instrument illustrated in FIG. 8.

Referring to FIG. 13, the bone engaging portion 202 is threadingly advanced into the iliac crest IC of the pelvic bone P until the conical surface 232 of the adjustable stop member 206 engages the proximal end 64 of the cannula tube 52. Continued threading advancement of the bone engaging portion 202 into the bone will cause the teeth or serrations 68 formed at the distal end 66 of the cannula tube 52 to bite into the outer surface of the bone to firmly secure the mounting instrument 250 to the iliac crest IC. At this point, the bone engaging portion 202 extends into the iliac crest IC at the proper depth or distance d. With the bone engaging portion 202 threadingly engaged to bone and the adjustable stop member 206 engaged tightly against the proximal end 64 of the cannula tube 52, the mounting instrument 250 in turn becomes rigidly attached to the iliac crest IC. The handle 240 of the bone anchor 200 may then be removed from the end portion 224 of the shaft 204 by axially displacing the coupler 242 away from the handle 240. Removal of the handle 240 from the remainder of the bone anchor 200 provides the mounting device 250 with a lower profile, thereby reducing the likelihood of interfering with or otherwise hindering the surgeon or other medical personnel during the surgical procedure. Upon completion of the surgical procedure, the handle 240 may once again be re-inserted back onto the end portion 224 of the shaft 204 to provide a means for unthreading and removing the bone anchor 200 from the iliac crest IC.

Following rigid attachment of the mounting instrument 250 to the iliac crest IC, the reference frame 300 is connected to the mounting device 250 by engaging the coupling mechanism 320 of the reference frame 300 with the coupling mechanism 54 of the cannula 50. Specifically, the radially-extending splines 328 of the coupling mechanism 320 (FIGS. 9 and 10) are engaged with the radially-extending splines 76 of the coupling mechanism 54 (FIGS. 3 and 4) in an interdigitating manner. With the radially-extending splines 76, 328 intermeshed with one another, the threaded stem portion 84 of the fastener 72 is threaded into the threaded opening 330 of the coupling mechanism 320 to fixedly mount the reference frame 300 at a select angular disposition relative to the mounting instrument 250. Specifically, the U-shaped frame member 302 of the reference frame 300 extends along a transverse axis T that is arranged at an angle $\alpha$ relative to the longitudinal axis L of the mounting instrument 250. As should be apparent, the interdigitating engagement between the coupling mechanism 54 and the coupling mechanism 320 permits the reference frame 300 to be selectively disposed within a range of angles $\alpha$ relative to the mounting instrument 250. In one embodiment of the invention, the angle a falls within a range of about 90 degrees to about 150 degrees. In a more specific embodiment, the angle $\alpha$ is about 130 degrees. It should be understood, however, that the angle a may take on other values as well, including angles less than 90 degrees and greater than 150 degrees. As should also be apparent, the reference frame 300 may be easily removed from the mounting instrument 250 by simply unthreading the fastener 72 from the threaded opening 330.

With the reference frame 300 rigidly secured to the mounting instrument 250, the patient is scanned and imaged with a CAT scan, an MRI or any other suitable scanning procedures to generate a field of view sufficiently large to display the spinal anatomy and the reference frame 300. The scanned radiographic image is then loaded into a surgical navigation system processor (not shown). Typically, the scanning process takes place in a scanning room or a similar facility. Following scanning, the patient is transferred to an operating room or a similar facility. Once in the operating room, the scanned radiographic image may be displayed on a monitor for viewing by the surgeon before and/or during an image-guided surgical procedure. In one embodiment of the invention, the pre-procedural scanned image is used throughout the image-guided surgical procedure. However, it should be understood that in other embodiments of the invention, intra-procedural scans may be taken to verify or update the pre-procedural scanned image.

Figure 14:
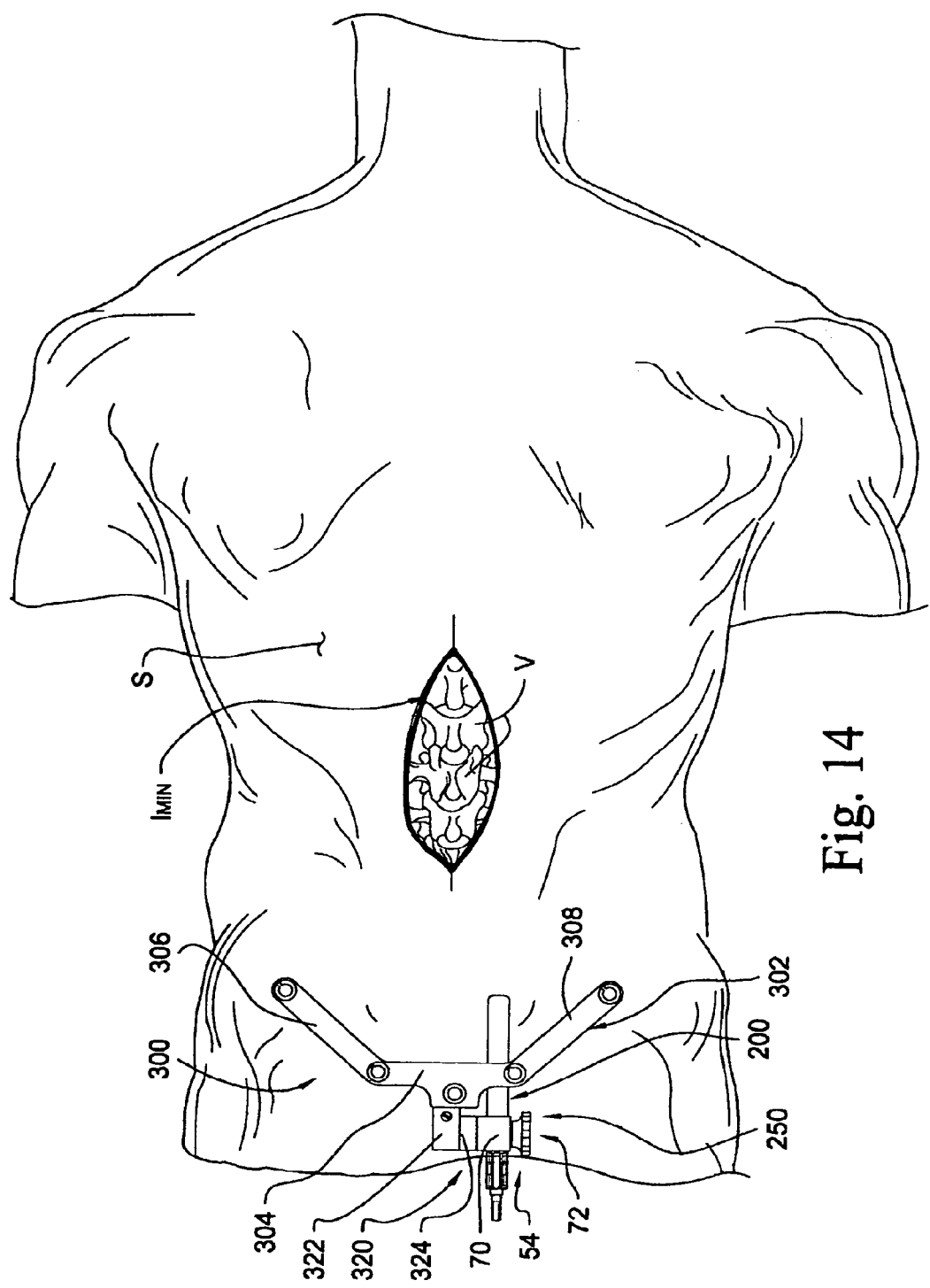
FIG. 14 is a top view of the patient illustrated in FIG. 13, illustrating coupling of the surgical navigation reference device to the mounting instrument, and also illustrating the formation of a minimally invasive surgical incision above the lumbar region of the spinal column at a location remote from the anchoring location.

Referring to FIG. 14, in one embodiment of the present invention, a surgical incision $I_{MIN}$ is formed at a location remote from the anchoring location of the reference frame 300. Positioning of the reference frame 300 at a location remote from the surgical incision $I_{MIN}$ provides the surgeon with an unobstructed area above and adjacent the surgical site. As a result, the surgeon may perform the surgical procedure without having to manipulate around or be encumbered/hindered by the reference frame 300 and/or the mounting instrument 250. For purposes of comparison, the prior art navigation system illustrated in FIG. 2 positions the reference frame 20 directly above the surgical incision I, thereby creating a structural obstruction to the surgical site which may interfere with the surgical procedure or otherwise hinder the surgeon during the surgical procedure.

In the illustrated embodiment, the surgical incision $I_{MIN}$ is formed adjacent the patient's spinal column for performing an image-guided surgical procedure on or around one or more of the patient's vertebrae V. It should be understood, however, that the surgical incision $I_{MIN}$ may be formed at other locations for performing an image-guided surgical procedures on or around other anatomical components. After forming the surgical incision $I_{MIN}$, the surgeon may perform an image-guided surgical procedure on the patient through the surgical incision $I_{MIN}$. However, in applications involving fluoroscopic surgery or other types of percutaneous surgery, the image-guided surgical procedure may be performed through a small opening formed through the skin S of the patient, thereby eliminating the need to form a surgical incision $I_{MIN}$.

Notably, the size of the surgical incision $I_{MIN}$ need only be large enough to provide the surgeon with sufficient access to the surgical site. In this manner, the image-guided surgical procedure may be performed in a minimally invasive manner. For purposes of comparison, the image navigation system illustrated in FIG. 2 requires a large surgical incision that must not only provide sufficient access to the surgical site, but which must also be sized to accommodate anchoring of the reference frame 20 to the vertebra $V_A$. As should be appreciated, large surgical incisions are highly invasive and can result in increased trauma, blood loss, post-operative pain, and a lengthy recovery period.

Figure 2:
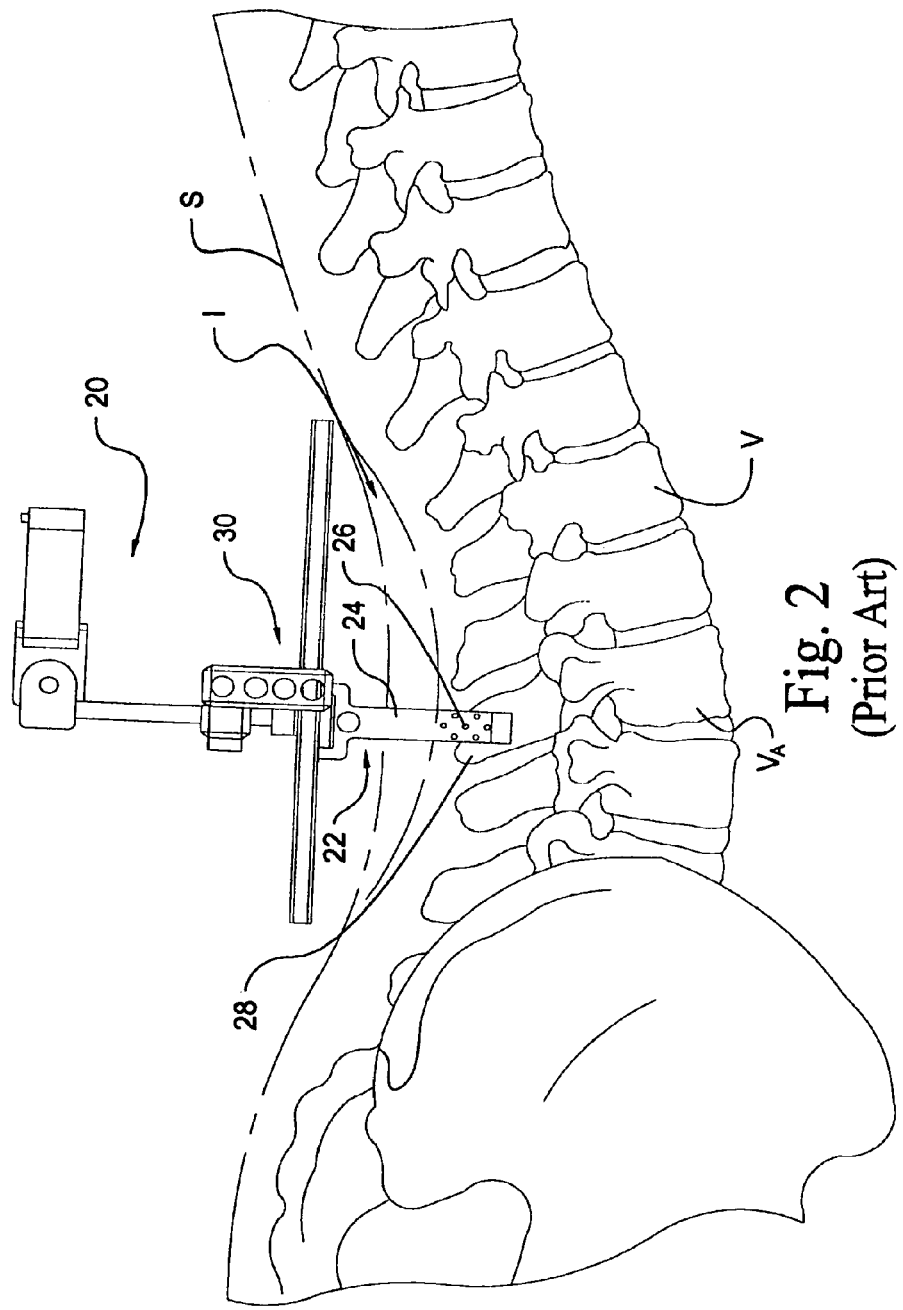
FIG. 2 is a side view of the spinal column of the patient illustrated in FIG. 1, illustrating the clamping of a surgical navigation reference device to the spinous process of a vertebra.

In a preferred embodiment of the invention, the surgical incision $I_{MIN}$ is formed subsequent to anchoring of the reference frame 300 to the patient. In this manner, the surgeon need not necessarily be present during acquisition of the radiographic images and/or during other pre-operative procedures. Moreover, anchoring of the reference frame 300 to the iliac crest IC can be performed in an environment requiring a lesser degree of sterilization than that normally associated with the formation of a surgical incision and/or commencement of a surgical procedure. For example, full draping is not necessarily required during anchoring of the reference frame 300 to the patient and/or during acquisition of the radiographic images. For purposes of comparison, as illustrated in FIG. 2, anchoring of the reference frame 20 to the vertebra $V_A$ must be done in an intra-procedural following formation of the surgical incision I by the surgeon. As a result, the overall length of the surgical procedure is increased, thereby tending to increase the overall risk of infection. Moreover, following formation of the surgical incision I, the surgeon must wait around while other medical personnel acquire the radiographic images of the vertebra $V_A$, thereby resulting in inefficient use of the surgeon's time.

As would be apparent to one of skill in the art, during the initial stage of an image-guided surgical procedure, the surgeon touches a surgical instrument or pointer having a tracking emitter attached thereto to the calibration divot 314 to register the location of the reference frame 300 in the navigation system processor. Since the reference frame 300 is maintained in a substantially fixed position relative to the patient's spinal anatomy, the particular position of spinal components may also be registered in the navigation system processor. Based upon the registered position of the spinal components, the image navigation processor generates and illustrates the pre-procedural scanned image of the spinal components on a monitor that is viewable by the surgeon. For additional positioning information, wires or screws equipped with emitters can be affixed to one or more spinal elements to provide data corresponding to the actual position and orientation of the patient's spinal column. This real-time measured data can be compared with the scanned data and, if necessary, the position and/or orientation of the patient may be manipulated by the surgeon until the measured data corresponds to that of the scanned data.

As would be apparent to one of skill in the art, the position of a surgical instrument fitted with one or more emitters can be tracked in three-dimensional space relative to the patient's spinal anatomy in real time. Such surgical instruments include, for example, distractors, drills, reamers, drivers, forceps, or any other type of surgical instrument that would be apparent to one of skill in the art. Various medical and surgical procedures may then be performed on the patient's spinal anatomy by using image-guided technology. For example, a discectomy may be performed on one or more of the patient's vertebrae V via an image-guided surgical procedure to remove at least a portion of the natural intervertebral disc. Additionally, endoscopes or biopsy probes can be inserted into the patient's spine via the image-guidance system. Various types of spinal implants may also be inserted into or attached to one or more of the vertebrae V via an image-guided surgical procedure. As would be apparent to one of skill in the art, the implant may itself be fitted with one or more emitters such that the implant may tracked in space relative to the spinal anatomy. Such implants include, for example, fusion devices, spacers, artificial discs, screws, rods, hooks, plates, wires, or other types of implants or devices typically used in association with treatment of the spine.

Figure 17:
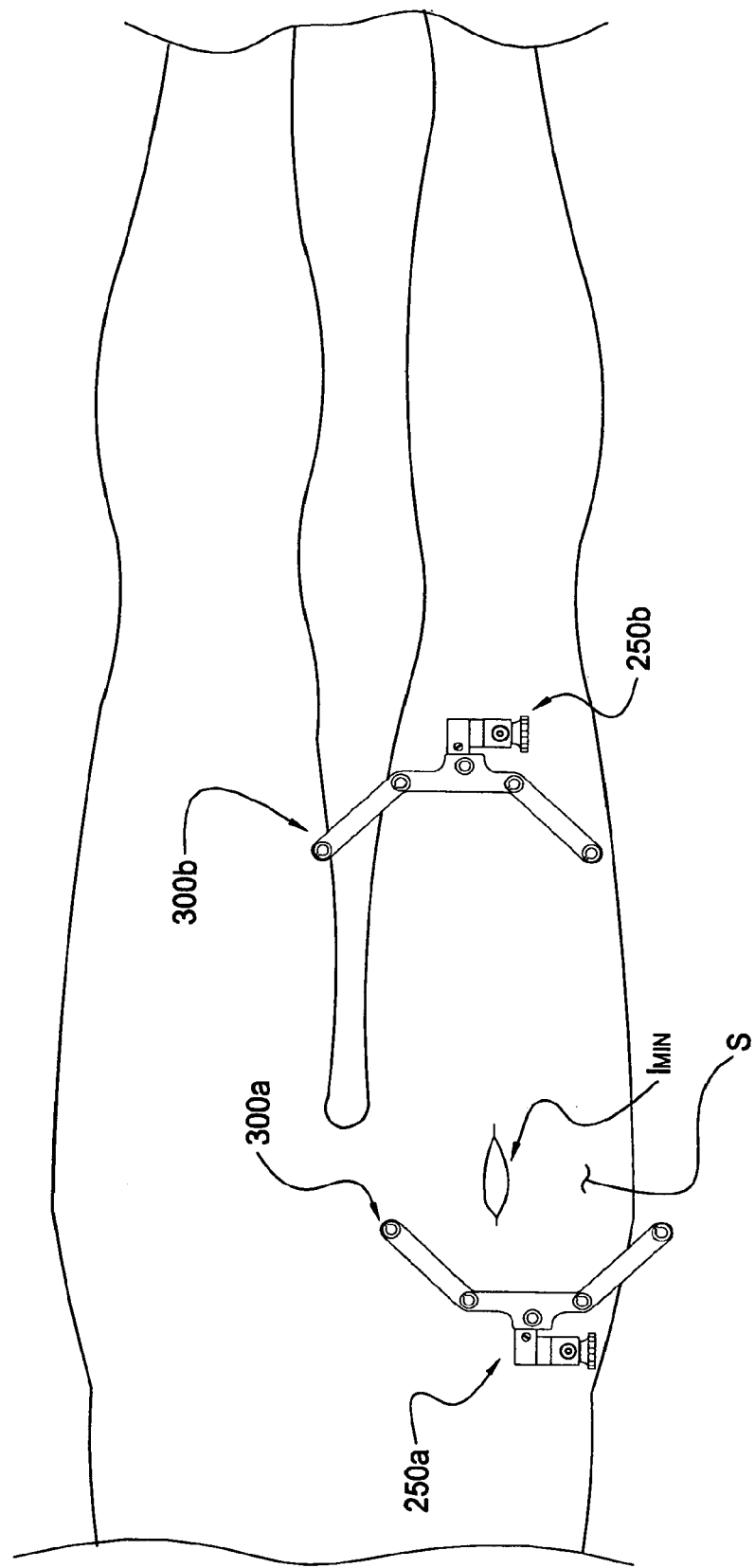
FIG. 17 is a top view of the patient illustrated in FIG. 16, illustrating percutaneous anchoring of the surgical navigation reference devices to the patient, and also illustrating the formation of a minimally invasive surgical incision adjacent the hip joint at a location remote from the percutaneous anchoring locations.

Referring to FIGS. 15-17, shown therein is a method for mounting two image navigation reference frames 300a, 300b to a patient according to a further form of the present invention. In one embodiment of the invention, the image navigation reference frames 300a, 300b are used to perform an image-guided surgical procedure adjacent a patient's hip joint J. In a specific embodiment, the image navigation reference frames 300a, 300b are used in association with an image-guided total hip replacement procedure. However, it should be understood that other types of surgical procedures are also contemplated, including partial hip replacement procedures or other surgical procedures associated with the hip joint J. It should also be understood that the reference frames 300a, 300b may be used in association with other types of image-guided surgical procedures, such as, for example, surgical procedures on other anatomical joints, including the knee, ankle, elbow or wrist joints.

A total or partial hip replacement procedure typically involves the removal and preparation of various portions of the hip joint to accommodate receipt of a hip prosthesis (not shown). A hip prosthesis is typically made up of two components; namely, an acetabular component and a femoral component. The acetabular component, generally referred to as the socket or shell portion, is configured to replace the acetabulum portion of the pelvic bone. The femoral component, generally referred to as the stem and ball portion, is configured to replace the femoral head portion of the femur. It should be understood that various types and configurations of prosthetic hip devices are well known in the art, and that a number of such devices may be used in association with the present invention as would occur to one of skill in the art.

In the past, total or partial hip replacement procedures have typically involved the formation of one or more relatively large surgical incisions to provide access to the hip joint. Once access to the hip joint is achieved, the femoral head is disengaged from the acetabulum. The femoral head is then removed by cutting through the femoral neck with a saw or another type of cutting instrument. After the femoral head is removed, the cartilage and/or other tissue is removed from the acetabulum using a drill or reamer. The reamer forms the bone into a hemispherical shape that is sized and configured to accept the socket portion of the acetabular component. Rasps may used to shape and hollow out the femoral canal to match the shape of the stem portion of the femoral component. Once the appropriate size and shape of the femoral canal is attained, the stem portion of the femoral component is inserted into the femoral canal and the ball portion of the femoral component is engaged within the socket portion of the acetabular component. Additional details associated with a total or partial hip replacement procedure are well known to those of skill in the art, and therefore need not be discussed in further detail herein.

As discussed above, total or partial hip replacement procedures commonly involve the formation of one or more relatively large surgical incisions through the skin of the patient to provide access to the hip joint. The size of the surgical incisions is largely dictated by the space requirements for accommodating the manipulation and/or placement of various surgical instruments and implant components required for the surgical procedure, and to provide the surgeon with direct visualization of the anatomical components associated with the hip joint as well as direct visualization of the components of the hip prosthesis upon implantation. However, large surgical incisions are highly invasive and can result in increased trauma, blood loss, post-operative pain, and a lengthy recovery period. As a result, minimally invasive surgical equipment and procedures have been developed to reduce the size and/or the number of surgical incisions. However, as should be appreciated, reducing the size of the surgical incisions also has the effect of decreasing the surgeon's ability to directly visualize the internal anatomy adjacent the surgical site as well as the components of the prosthetic device upon implantation. The use of an image navigation system may therefore be helpful to aid the surgeon in performing various surgical steps and procedures involving the preparation of the anatomy and/or the insertion and manipulation of surgical instruments and implant components.

Hip replacement procedures are typically performed with the patient situated in either a supine position (e.g., facing up) or in a lateral position (e.g., facing sideways). Referring to FIGS. 15 and 16, in the illustrated embodiment of the invention, the patient is situated in a supine position with an image navigation reference frame positioned on either side of the hip joint J. The use of two image navigation reference frames positioned on either side of the hip joint J is preferred since the femur F is not directly connected to the pelvic bone P, thereby permitting relative rotation and/or displacement between the femur F and the pelvic bone P during the surgical procedure. However, it should be understood that the use of a single image navigation reference frame is also contemplated as falling with the scope of the present invention, including embodiments where an image navigation reference frame is mounted only to the femur F or only to the pelvic bone P.

In a preferred embodiment of the invention, the image navigation reference frame 300a is mounted to the patient's pelvic bone P while the image navigation reference frame 300b is mounted to the patient's femur F. In one embodiment of the invention, the image navigation reference frame 300a is mounted to the iliac region of the pelvic bone P, and more specifically to the iliac crest IC. If the patient is situated in a supine position, as shown in the FIGS. 15 and 16, the reference frame 300a is preferably mounted to the anterior superior region of the iliac crest IC. However, it should be understood that the reference frame 300a may alternatively be mounted to other regions of the iliac crest IC or to other portions of the pelvic bone P. If the patient is situated in a face down position, the reference frame 300a may be mounted to the posterior superior region of the iliac crest IC, as illustrated in FIG. 13, or to other regions of the pelvic bone P. Additionally, if the patient is situated in a lateral position (not shown), the reference frame 300a may be mounted to any portion of the iliac crest IC or to other regions of the pelvic bone P. In a further embodiment of the invention, the image navigation reference frame 300b is mounted to the distal portion of the femur F (adjacent the knee) to provide the surgeon with relatively uninhibited/unhindered access to the hip joint J. However, it should be understood that the reference frame 300b may alternatively be mounted to other portions of the femur F, including the mid-portion or proximal portion of the femur F. Additionally, although the reference frames 300a, 300b have been illustrated and described as being mounted to specific portions and locations of the patient's anatomy, it should be understood that the reference frames 300a, 300b may be anchored to other skeletal members and positioned adjacent other anatomical components.

In a preferred embodiment of the invention, the reference frames 300a, 300b are mounted to the pelvic bone P and to the femur F by way of the same devices and procedures illustrated and described above with regard to the reference frame 300. More specifically, in a preferred embodiment of the invention, the reference frames 300a, 300b are percutaneously mounted to the pelvic bone P and to the femur F. Similar to the procedure illustrated in FIG. 11 and described above, the insertion instrument 150 is percutaneously introduced through the skin S of the patient in a minimally invasive manner to position the distal end 66 of the cannula 50 into engagement with bone. The trocar 150 is removed from the cannula 50, thereby establishing a percutaneous portal through the patient's skin S to a location adjacent the bone, such as, for example, locations adjacent the iliac crest IC of the pelvic bone P and the distal end portion of the femur F. Additionally, similar to the procedure illustrated in FIGS. 12 and 13, the bone engaging portion 202 of a bone anchor 200 is inserted through the percutaneous portal established by the cannula 50 and is driven into secure engagement with bone. The adjustable stop member 206 is tightly engaged against the proximal end 64 of the cannula 50, thereby forming a pair of substantially rigid mounting device 250. Referring to FIGS. 15 and 16, the resulting mounting devices 250a, 250b are securely anchored to the iliac crest IC of the pelvic bone P and to the distal end portion of the femur F, respectively.

As illustrated in FIGS. 15 and 16, each of the reference frames 300a, 300b are connected to the mounting devices 250a, 250b, respectively, by engaging the coupling mechanism 320 of the reference frames 300a, 300b with the coupling mechanism 54 of the cannula 50, the details of which have been illustrated and described above with regard to the mounting device 250 and the reference frame 300. It should be understood that the reference frames 300a, 300b are configured and operate in a manner virtually identical to the reference frame 300 illustrated and described above. Additionally, as discussed above, other types and configurations of reference frames are also contemplated for use in association with the present invention as would occur to one of skill in the art.

Once the reference frames 300a, 300b are rigidly secured to the mounting devices 250a, 250b, which are in turn securely anchored to the pelvic bone P and the femur F, respectively, the patient is scanned and imaged with a CAT scan, an MRI or any other suitable scanning procedures to generate a field of view sufficiently large to display the hip joint J, the adjacent anatomy, and the reference frames 300a, 300b. The scanned radiographic image is then loaded into a surgical navigation system processor (not shown) and may be displayed on a monitor for viewing by the surgeon before and/or during an image-guided surgical procedure. In one embodiment of the invention, the pre-procedural scanned image is used throughout the image-guided surgical procedure. However, it should be understood that in other embodiments of the invention, intra-procedural scans may be taken to verify or update the pre-procedural scanned image.

Referring to FIG. 17, in one embodiment of the present invention, one or more minimally invasive surgical incisions $I_{MIN}$ are formed in an area adjacent the hip joint J, preferably at locations remote from the anchoring locations of the reference frames 300a, 300b. Positioning of the reference frames 300a, 300b at locations remote from the surgical incisions $I_{MIN}$ provides the surgeon with an unobstructed area above and adjacent the surgical site. As a result, the surgeon may perform the surgical procedure without having to manipulate around or be encumbered/hindered by the reference frames 300a, 300b and/or the mounting device 250a, 250b. After forming the surgical incisions $I_{MIN}$, the surgeon may then perform a minimally invasive, image-guided hip replacement procedure through the surgical incisions $I_{MIN}$. As indicated above, although the illustrated embodiment of the invention is specifically directed to an image-guided total or partial hip replacement surgical procedure, it should be understood that the surgical incisions $I_{MIN}$ may be formed at other locations for performing image-guided surgical procedures on or around other joints and/or anatomical components.

In a preferred embodiment of the invention, the surgical incisions $I_{MIN}$ are formed subsequent to the anchoring of the reference frames 300a, 300b to the patient. In this manner, the surgeon need not necessarily be present during acquisition of the radiographic images and/or during other pre-operative procedures. Moreover, anchoring of the reference frames 300a, 300b can be performed in an environment requiring a relatively lesser degree of sterilization compared with that normally associated with the formation of a surgical incision and/or the commencement of a surgical procedure. For example, full draping is not necessarily required during anchoring of the reference frames 300a, 300b to the patient and/or during acquisition of the radiographic images.

As would be apparent to one of skill in the art, during the initial stage of an image-guided surgical procedure, the surgeon may touch a surgical instrument or pointer having a tracking emitter attached thereto to a calibration divot to register the location of the reference frames 300a, 300b or other reference components in the navigation system processor (not shown). Since the reference frames 300a, 300b are maintained in a substantially fixed position relative to the pelvic bone P and to the femur F, respectively, the particular position and orientation of these anatomic structures may also be registered in the navigation system processor. The particular position and orientation of the pelvic bone P and the femur F may then be tracked and monitored throughout the surgical procedure. Based upon the registered position of the pelvic bone P and the femur F, the image navigation processor generates and illustrates the pre-procedural scanned image of these components on a monitor that is viewable by the surgeon. For additional positioning information, wires or screws equipped with emitters can be affixed to other bones or anatomic structures to provide additional data corresponding to the actual position and orientation of the patient's hip joint J. This real-time measured data can be compared with the scanned data and, if necessary, the position and/or orientation of the patient may be manipulated by the surgeon until the measured data corresponds to that of the scanned data.

A hip replacement procedure may then be performed with the aid of image-guided navigation technology. As would be apparent to one of skill in the art, the position of a surgical instrument fitted with one or more emitters can be tracked in two-dimensional or three-dimensional space relative to the patient's anatomy or other devices/components in real time. Such surgical instruments may include, for example, saws, drills, reamers, drivers, forceps, or any other type of surgical instrument that would be apparent to one of skill in the art for use in association with hip replacement procedures.

Additionally, the acetabular and femoral components of the hip prosthesis may be inserted into the patient and manipulated/adjusted to the appropriate position and/or orientation via an image-guided navigation system. Specifically, as would be apparent to one of skill in the art, the components of the hip prosthesis may be fitted with one or more emitters such that the components may tracked and navigated in two-dimensional or three-dimensional space relative to one another and/or relative to the pelvic bone P and the femur F. With regard to the acetabular component, the reference frame 300a is used as the primary means for tracking/navigating since the reference frame 300a is mounted in a substantially fixed position relative to the pelvic bone P to which the acetabular component is engaged. Similarly, the reference frame 300b is used as the primary means for tracking/navigating the femoral component since the reference frame 300b is mounted in a substantially fixed position relative to the femur F to which the femoral component is engaged. The use of image navigation technology is particularly advantageous in referencing the rotational position of the femoral component within the femoral canal relative to the femur F and the pelvic bone P. As should be appreciated, the precise rotational positioning and alignment of the femoral component, and more particularly the ball portion of the femoral component, is crucial to the overall success of a hip replacement procedure.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method of mounting a surgical navigation reference device to a patient for performing an image-guided surgical procedure adjacent the patient's spinal column, comprising:
   providing a bone anchor;
   anchoring the bone anchor to bone at a location remote from the patient's spinal column;
   coupling the reference device to the bone anchor to mount the reference device in a substantially fixed position relative to the patient's spinal column; and
   performing an image-guided surgical procedure adjacent the patient's spinal column.

2. The method of claim 1, wherein the anchoring comprises anchoring the bone anchor to a portion of the patient's pelvic bone.

3. The method of claim 2, wherein the portion of the pelvic bone is the iliac region of the pelvic bone.

4. The method of claim 3, wherein the portion of the pelvic bone is the iliac crest.

5. The method of claim 1, further comprising percutaneously inserting the bone anchor into the patient prior to the anchoring.

6. The method of claim 5, wherein the percutaneously inserting comprises:
   providing a cannula having a proximal end and a distal end;
   providing a trocar having a distal end portion;
   positioning the trocar within the cannula with the distal end portion of the trocar extending beyond the distal end of the cannula;
   percutaneously introducing the cannula into the patient;
   removing the trocar from the cannula; and
   inserting a bone engaging portion of the bone anchor through the cannula and into engagement with bone.

7. The method of claim 1, further comprising:
   forming a minimally invasive surgical incision at a location remote from the anchoring location; and
   performing the image-guided surgical procedure through the minimally invasive surgical incision.

8. The method of claim 7, wherein the minimally invasive surgical incision is formed subsequent to the anchoring.

9. The method of claim 1, wherein the image-guided surgical procedure is a minimally invasive image-guided surgical procedure on a portion of the patient's spinal column.

10. A method of percutaneously mounting a surgical navigation reference device to a patient for performing an image-guided surgical procedure, comprising:
    providing a cannula having a proximal end and a distal end, a trocar having a distal end portion, and a bone anchor having a bone engaging portion;
    positioning the trocar within the cannula with the distal end portion of the trocar extending beyond the distal end of the cannula;
    percutaneously introducing the cannula into the patient;
    removing the trocar from the cannula;
    inserting the bone engaging portion of the bone anchor through the cannula;
    anchoring the bone engaging portion of the bone anchor to bone; and
    coupling the surgical navigation reference device to the bone anchor.

11. The method of claim 10, further comprising securely engaging the distal end of the cannula against the bone to substantially prevent displacement of the cannula relative to the bone.

12. The method of claim 11, wherein the coupling comprises securely engaging the bone anchor with the cannula and connecting the surgical navigation reference device to the cannula.

13. The method of claim 10, wherein the bone engaging portion of the bone anchor is threaded and wherein the anchoring comprises threading the bone engaging portion of the bone anchor into the bone.

14. The method of claim 13, wherein the bone engaging portion of the bone anchor is self-tapping, and wherein the threading comprises cutting threads along an opening in the bone.

15. The method of claim 13, wherein the bone engaging portion of the bone anchor is self-drilling and self-tapping, and wherein the threading comprises forming a threaded opening in the bone.

16. The method of claim 10, further comprising performing a percutaneous image-guided surgical procedure on the patient.

17. The method of claim 10, further comprising;
    forming a minimally invasive surgical incision at a location remote from the anchoring location; and
    performing an image-guided surgical procedure on the patient through the minimally invasive surgical incision.

18. The method of claim 17, wherein the surgical incision is formed subsequent to the anchoring.

19. The method of claim 10, wherein the anchoring comprises anchoring the bone engaging portion of the bone anchor to bone at a location remote from the patient's spinal column; and
    further comprising performing a minimally invasive image-guided surgical procedure on a portion of the patient's spinal column.

20. The method of claim 19, wherein the anchoring comprises anchoring the bone engaging portion of the bone anchor to a portion of the patient's pelvic bone.

21. The method of claim 20, wherein the portion of the pelvic bone is the iliac crest.

22. The method of claim 10, wherein the anchoring comprises anchoring the bone engaging portion of the bone anchor to a portion of the patient's pelvic bone; and
    further comprising performing a minimally invasive image-guided surgical procedure on the patient's hip joint.

23. The method of claim 22, wherein the portion of the patient's pelvic bone is the iliac crest.

24. The method of claim 22, further comprising percutaneously mounting another of the surgical navigation reference device to the patient's femur.

25. Instrumentation for performing an image-guided surgical procedure on a patient, comprising:
    a cannula having a proximal end and a distal end;
    a trocar positioned within said cannula with a distal end portion of said trocar extending beyond said distal end of said cannula to form an insertion device adapted for percutaneous introduction into the patient;
    a bone anchor having a bone engaging portion insertable through said cannula and adapted for anchoring to bone, said bone anchor cooperating with said cannula to form a mounting device; and
    a surgical navigation reference device adapted for coupling to said mounting device to percutaneously mount the reference device to the patient.

26. The instrumentation of claim 25, wherein said distal end of said cannula includes at least one anchoring element adapted to securely engage said cannula against the bone to substantially prevent displacement of said cannula relative to the bone.

27. The instrumentation of claim 25, wherein said surgical navigation reference device is a reference frame assembly.

28. The instrumentation of claim 25, wherein said distal end portion of said trocar is pointed to facilitate percutaneous introduction of said insertion device into the patient.

29. The instrumentation of claim 25, wherein said trocar includes a stop member engagable against said proximal end of said cannula to position said distal end portion of said trocar relative to said distal end of said cannula.

30. The instrumentation of claim 25, wherein said bone anchor includes a stop member engagable against said proximal end of said cannula to limit displacement of said bone engaging portion beyond said distal end of said cannula.

31. The instrumentation of claim 30, wherein said stop member is adjustably positionable relative to said bone anchor to selectively limit displacement of said bone engaging portion beyond said distal end of said cannula.

32. The instrumentation of claim 25, wherein said bone engaging portion of said bone anchor is self-tapping.

33. The instrumentation of claim 32, wherein said bone engaging portion of said bone anchor is self-drilling.

34. The method of claim 10, wherein said anchoring includes rotating said bone anchor until a stop member attached to said first anchor abuts a portion of said cannula, whereby over-insertion and under-insertion of said first anchor into the bone is guarded against.

\* \* \* \* \*